US012805544B2

(12) United States Patent
Zhou et al.

(10) Patent No.: US 12,805,544 B2
(45) Date of Patent: Nov. 24, 2026

(54) LOW LIPID CONTENT OAT PROTEIN COMPOSITION WITHOUT TRACES OF ORGANIC SOLVENT

(71) Applicant: ROQUETTE FRERES, Lestrem (FR)

(72) Inventors: Leon Zhou, Geneva, IL (US); Kerry Campbell, Geneva, IL (US); Ron Cheng, Geneva, IL (US)

(73) Assignee: Roquette Freres, Lestrem (FR)

(*) Notice: Subject to any disclaimer, the term of this patent is extended or adjusted under 35 U.S.C. 154(b) by 701 days.

(21) Appl. No.: 17/597,222

(22) PCT Filed: Jul. 2, 2020

(86) PCT No.: PCT/EP2020/068658
§ 371 (c)(1),
(2) Date: Dec. 29, 2021

(87) PCT Pub. No.: WO2021/001478
PCT Pub. Date: Jan. 7, 2021

(65) Prior Publication Data
US 2022/0240540 A1 Aug. 4, 2022

(30) Foreign Application Priority Data
Jul. 2, 2019 (EP) .................................... 19315052

(51) Int. Cl.

| | |
|---|---|
| ***A61D 5/00*** | (2006.01) |
| ***A23D 9/00*** | (2006.01) |
| ***A23J 1/12*** | (2006.01) |
| ***A23K 50/40*** | (2016.01) |
| ***A23L 7/10*** | (2016.01) |
| ***A23L 33/17*** | (2016.01) |
| ***A23L 33/185*** | (2016.01) |
| ***A61D 7/00*** | (2006.01) |
| *A23K 10/14* | (2016.01) |
| *A23K 10/30* | (2016.01) |
| *A23K 20/147* | (2016.01) |
| *A61G 19/00* | (2006.01) |
| *A61K 8/64* | (2006.01) |
| *A61K 36/899* | (2006.01) |
| *A61K 38/16* | (2006.01) |

(52) U.S. Cl.
CPC ................ *A23J 1/125* (2013.01); *A23D 9/00* (2013.01); *A23L 7/10* (2016.08); *A23L 33/17* (2016.08); *A23L 33/185* (2016.08); *A23K 10/14* (2016.05); *A23K 10/30* (2016.05); *A23K 20/147* (2016.05); *A61G 19/00* (2013.01); *A61K 8/645* (2013.01); *A61K 36/899* (2013.01); *A61K 38/168* (2013.01)

(58) Field of Classification Search
CPC ... A23J 1/125; A23D 9/00; A23L 7/10; A23L 33/17; A23L 33/185; A23K 10/14; A23K 10/30; A23K 20/147; A61K 8/645; A61K 36/899; A61K 38/168; A61K 2236/00; A61K 2800/10; A61Q 19/00; A23V 2002/00; A23V 2250/5484
See application file for complete search history.

(56) References Cited

U.S. PATENT DOCUMENTS

| | | | |
|---|---|---|---|
| 5,525,151 | A | 6/1996 | Lenz et al. |
| 10,259,851 | B2 | 4/2019 | Gagnon et al. |
| 2009/0155444 | A1 | 6/2009 | Yakubu |
| 2013/0183404 | A1 | 7/2013 | Whalen |
| 2021/0284683 | A1 | 9/2021 | Hasjim et al. |

FOREIGN PATENT DOCUMENTS

| | | | |
|---|---|---|---|
| CN | 106085589 | A | 11/2016 |
| CN | 107307246 | A | 11/2017 |
| EP | 0051943 | A2 | 5/1982 |
| EP | 1706001 | A1 | 10/2006 |
| EP | 2120604 | A1 | 11/2009 |
| WO | 2009076136 | A1 | 6/2009 |
| WO | 2014137606 | A1 | 9/2014 |

OTHER PUBLICATIONS

Li et al., Sensitivity of oat protein solubility to changing ionic strength and pH, Journal of Food Science, vol. 86 Iss. I, 2021 (Year: 2021).*
Comino et al., "Identification and molecular characterization of oat peptides implicated on coeliac immune response," Food & nutrition research 60.1 (2016): 30324.

* cited by examiner

*Primary Examiner* — Nikki H. Dees
*Assistant Examiner* — Stephanie R Gerla

(57) ABSTRACT

The invention pertains to the field of oat protein compositions and production method thereof. In particular, the present invention is directed to an oat protein composition having low lipid content and which does not contain traces of organic solvent and to the production method thereof.

12 Claims, No Drawings

LOW LIPID CONTENT OAT PROTEIN COMPOSITION WITHOUT TRACES OF ORGANIC SOLVENT

TECHNICAL FIELD

The invention pertains to the field of oat protein compositions and production method thereof. In particular, the present invention is directed to an oat protein composition having low lipid content and which does not contain traces of organic solvent and to the production method thereof.

BACKGROUND ART

Oats are a well-known source of a wide variety of useful products. Examples of such products are flour, starch, protein isolate and concentrate, protein-enriched flour, bran, gum and oil. Traditional techniques used in the cereal grain processing industry are frequently difficult to use with oats because of process problems relating to the presence of lipids in the oats. Moreover, unless the oats are de-oiled prior to milling, milling processes would result in the formation of flour and protein fractions containing lipids, which may result in the development of rancidity on storage of the flour and protein.

The most widely used technique consists in a first de-oiling made with help of organic solvents like hexane or ethanol. Man skilled in the art is aware for example of EP0051943 from DUPONT which teaches the use of aliphatic hydrocarbon solvent to remove lipids from oat flours. Main drawbacks of such technologies are industrial use of organic solvent, associated explosion risks and spoilage, and residual levels of lipids in final products.

Such risks seem so important that the main current commercial product called PROATEIN® is currently produced without de-oiling. EP1706001 is only based on the use of amylases and centrifugal separation. As disclosed in the example part, such process leads to a composition having a lipid content above 10% by weight based on total weight.

To address these drawbacks, some alternative processes have been recently proposed. Such processes are based on the use of supercritical $CO_2$. Man skilled in the art is aware of EP2120604 from VALTION TEKNILLINEN. However, to reach a high level of de-oiling, flour need to be processed and grinded, thereby leading to a mean particle size of protein below 10 microns (see paragraph 0047 of EP2120604). This process leads to a superfine size protein powder which is not desirable in some applications, but also which is difficult to handle in industrial plants, mainly due to dust formation and explosion hazard. Another major industrial problem linked to particles having a size below 10 microns is that the cyclone and filtration systems needed to recover such small particles are expensive and difficult to operate efficiently and/or effectively.

US 2009/0155444 A1 discloses an extrudate made from soy protein and oat flour. It does not describe an oat protein composition.

The document Brückner-Gühmann et al. (Foaming characteristics of oat protein and modification by partial hydrolysis, European Food Research and Technology, Vol. 244, n°12, 28 Aug. 2018, pages 2095-2106) describes the production of an oat protein isolate using an oat protein concentrate as a starting material, using a step of alkaline extraction of this concentrate, a step of separation of the protein into the supernatant and a step of lyophilisation of this supernatant to produce the oat protein isolate powder. This article explores the functionality of foaming of the obtained protein isolate. This document does not disclose the mean particle size of the oat protein composition obtained.

The objective of the present patent application is to overcome these problems and thus to propose a new process that improves prior art existing techniques thereby delivering a unique oat protein powder.

DESCRIPTION OF EMBODIMENTS

A first embodiment of the present invention is an oat protein composition characterized in that said composition does not contain traces of organic solvent, has residual lipid content below 10% by weight on dry matter based on the total dry weight of the oat protein composition and has a mean particle size greater than 10 microns.

A second embodiment is a process for producing an oat protein composition which has a residual lipid content below 10% by weight on dry matter based on the total dry weight of the oat protein composition, which can be the oat protein composition of the present invention defined hereabove, characterized in that the process comprises the following steps:

1) Preparing oat seeds or provide a protein rich flour;
2) In the case of using oat seeds in step 1, grinding oat seeds of step 1 until obtaining a protein rich flour;
3) Mixing the protein rich flour of step 1 or 2 with water until obtaining a protein rich suspension;
4) Adjunction of an amylase enzyme to the protein rich suspension of step 3 thereby hydrolyzing the protein rich suspension;
5) Optionally separating by centrifugation the hydrolyzed protein rich suspension of step 4 until obtaining a heavy layer comprising fibers and a light layer comprising proteins;
6) Adjunction of polysorbate to the hydrolyzed protein rich suspension of step 4 or optionally to the light layer comprising proteins of step 5;
7) Separating by centrifugation the protein rich suspension comprising polysorbate or light layer comprising proteins of step 6 in an heavy layer containing proteins and a light layer containing soluble compounds including lipids; and
8) Optionally drying the heavy layer containing proteins of step 7.

A third and last embodiment are industrial uses of protein composition of the invention, preferably in food, feed, pharmaceutical and cosmetic fields.

The present invention will be better understood with the following detailed description.

DESCRIPTION OF DETAILED EMBODIMENTS

A first embodiment of the present invention is an oat protein composition characterized in that said composition does not contain traces of organic solvent, has residual lipid content below 10% by weight on dry matter based on the total dry weight of the oat protein composition and has a mean particle size greater than 10 microns.

By "a composition that does not contain traces of organic solvent" it is meant a composition that contains less than 100 ppm of solvent, preferably less than 10 ppm of organic solvent and more preferably a composition that does not contain organic solvent at all.

By "organic solvent", it is meant solvent based on compounds that contain carbon. On the opposite, inorganic solvents which are allowed in this invention do not contain carbon. A typical inorganic solvent allowed in the present invention is water.

"Oat" in the present application must be understood as a cereal plant belonging to the botanical genus *Avena*. This genus can be divided in wild and cultivated species which have been cultivated for thousands of years as a food source for humans and livestock. The cultivated species contain:

- *Avena sativa*—the most cultivated specie, commonly referred to as "oats".
- *Avena abyssinica*—the Ethiopian oat, native to Ethiopia, Eritrea, and Djibouti; naturalized in Yemen and in Saudi Arabia
- *Avena byzantina*, a minor crop in Greece and Middle East; introduced in Spain, Algeria, India, New Zealand, South America, etc.
- *Avena nuda*—the naked oat or hulless oat, which plays the same role in Europe as does A. *abyssinica* in Ethiopia. It is sometimes included in *A. sativa* and was widely grown in Europe before the latter replaced it. As its nutrient content is somewhat better than that of the common oat, A. *nuda* has increased in significance in recent years, especially in organic farming.
- *Avena strigosa*—the lopsided oat, bristle oat, or black oat, grown for fodder in parts of Western Europe and Brazil.

In a preferred embodiment, oat must be understood in the present application as *Avena nuda*, naked oat or hulless oat.

In a preferred embodiment, oat protein composition is a protein concentrate, or a protein isolate. The oat protein composition can thus have around 40% by weight of protein or above, based on dry matter based on the total dry weight of the oat protein composition, for example from around 40 to 85%.

In the present application, "protein concentrate" must be understood as an oat protein composition which contains from 40% to 70%, preferably from 50% to 60% by weight of protein on dry matter based on the total dry weight of the oat protein composition.

In the present application, "protein isolate" must be understood as an oat protein composition which contains more than 70%, preferably more than 80% by weight of protein on dry matter based on the total dry weight of the oat protein composition.

Various protocols can be used from prior art in order to quantify the protein content. In the present application, a preferred method to quantify the protein content consists of 1) analyzing nitrogen content in the composition using the Kjeldhal method and 2) multiplying the nitrogen content by 6,25 factor (which represent the average quantity of nitrogen in protein).

In the present application "protein" must be understood as molecules, consisting of one or more long chains of amino-acid residues. In the present application, proteins can be native proteins or modified proteins, including hydrolyzed proteins. These proteins can be present in different concentrations, including protein isolates or protein concentrates. Oats are the only cereal containing avenalin as globulin or legume-like protein, as the major storage protein (80% by weight). Globulins are characterized by their solubility in dilute saline as opposed to the more typical cereal proteins, such as gluten and zein which is a prolamine. The minor protein of oat is the prolamine which is called avenin.

In the present application "lipid" must be understood as molecules that are soluble in nonpolar solvents. Lipids include fatty acids, waxes, sterols, fat-soluble vitamins (such as vitamins A, D, E, and K), monoglycerides, diglycerides, triglycerides, and phospholipids. Oats, after corn, have the highest lipid content of all the cereals, i.e. greater than 10% by weight for some oats and as high as 17% by weight for some maize cultivars in comparison to about 2-3% by weight for wheat and most other cereals. The polar lipid content of oats (about 8-17% by weight glycolipid and 10-20% by weight phospholipid or a total lipid polar content of about 33% by weight) is greater than that of other cereals, since much of the lipid fraction is contained within the endosperm.

In order to quantify residual lipids, every well-known methods from man skilled in the art can be used. Preferably, the Test A based on the CEM method is used. The CEM method is based on a NMR analysis and gives an extractible lipid content. In the Test A based on the CEM method, the sample is simply introduced in the apparatus and, following the user manual, the analysis is launched and the result is obtained very quickly.

The oat protein composition presents advantageously a mean particle size greater than 20 microns, preferably greater than 30 microns, more preferably greater than 40 microns. The oat protein composition presents advantageously a mean particle size lower than 300 microns, preferably lower than 200 microns, more preferably lower than 150 microns.

The oat protein composition can comprise from 0.1 to 10% by weight of starch on dry matter based on the total dry weight of the oat protein composition, preferably from 0.5 to 6%, more preferably from 1 to 4%. Starch content of the composition can be determined using AOAC Official Method 996.11, Starch (Total) in Cereal Products.

The oat protein composition can comprise a total dietary fiber going from 0.1 to 10% by weight of fiber on dry matter based on the total dry weight of the oat protein composition, preferably from 0.5 to 6%, more preferably from 1 to 4%. In the present application, fiber content can be determined using AOAC Official Method 2017.16, Total Dietary Fiber in Foods and Food Ingredients. One of the dietary fibre generally presents in the composition is beta-glucans.

The oat protein composition can comprise, based on the total weight of the proteins in the composition, less than 50% of proteins having a molecular weight of 10 kDa and less, advantageously less than 30%, preferably less than 10%. In an embodiment, the oat protein composition comprises, based on the total weight of proteins in the composition:

- from 0.5 to 30% of proteins having a molecular weight of 300 kDa and more, advantageously from 5 to 15%,
- from 30 to 75% of proteins having a molecular weight of between 50 and 300 kDa, advantageously from 45 to 65%,
- from 10 to 50% of proteins having a molecular weight of between 10 and 50 kDa, advantageously from 25 to 45%,
- from 0.5 to 20% of proteins having a molecular weight of 10 kDa and less, advantageously from 1 to 10%, the sum making 100%.

An advantage of this preferred embodiment of the invention is that the molecular weight of the oat protein composition is high, which can provide different protein functionalities compared to low molecular weight oat protein composition such as described e.g. in the document Brückner-Gühmann et al.

The protein molecular weight (MW) distribution can be determined using Size Exclusion Chromatography. The protocols of preparation of the samples to analyze and of measurement using Size Exclusion Chromatography are included in the examples section below.

In the present application "particle size" must be understood as a notion introduced for comparing dimensions of solid, liquid or gaseous particles. The particle-size distribution (PSD) of a powder, or granular material, or particles dispersed in fluid, is a list of values or a mathematical function that defines the relative amount, typically by mass, of particles present according to size. Several methods can be used for measuring particle size and particle size distribution. Some of them are based on light, or on ultrasound, or electric field, or gravity, or centrifugation. The use of sieves is a common measurement technique. In the present application, the use of laser diffraction method is preferred. As for "mean particle size" (d 50) determined by laser diffraction, this mean particle size is a volume-weighted mean particle size. The man skilled in the art will be able to select a laser diffraction method allowing him to obtain an accurate mean particle size determination. An example of such method is indicated in the examples section.

In the present application, "dry matter" must be understood as the relative percentage by weight of solids based on total weight of the sample. Every well-known method can be used but desiccation method, which consists of estimating quantity of water by heating a known quantity of sample, is preferred. In the desiccation method:

a sample is prepared and its mass is weighed: $m_1$ (g), sample is put in an oven, to volatize water, until stabilization of the sample's mass. Preferably, during this step, the temperature is 105° C. at common atmospheric pressure.

final sample is weighed: $m_2$ (g)

The dry matter is calculated according to the following equation Dry matter=$(m_2/m_1)$*100.

A second embodiment of the present invention is a process for producing an oat protein composition which has a residual lipid content below 10% by weight on dry matter based on the total dry weight of the oat protein composition, which can be the oat protein composition as defined hereabove, characterized in that the process comprises the following steps:

1) Preparing oat seeds or provide a protein rich oat flour;
2) In the case of using oat seeds in step 1, grinding oat seeds of step 1 until obtaining a protein rich flour;
3) Mixing the protein rich flour of step 1 or 2 with water until obtaining a protein rich suspension;
4) Adjunction of an amylase enzyme to the protein rich suspension of step 3 thereby hydrolyzing the protein rich suspension;
5) Optionally separating by centrifugation the hydrolyzed protein rich suspension of step 4 until obtaining a heavy layer comprising fibers and a light layer comprising proteins;
6) Adjunction of polysorbate to the hydrolyzed protein rich suspension of step 4 or optionally to the light layer comprising proteins of step 5;
7) Separating by centrifugation the protein rich suspension comprising polysorbate or light layer comprising proteins of step 6 in an heavy layer containing proteins and a light layer containing soluble compounds including lipids; and
8) Optionally drying the heavy layer containing proteins of step 7.

Thus, the process of the present invention does not use organic solvents and allows obtaining a composition which does not contain traces of organic solvent.

The first step aims to provide oat seeds in a state that allows further steps. Oat seeds may be cultivated and/or commercially available. Oat seeds may then prepared including possible steps of sieving or dehulling.

Oats seeds may be dry- or wet-heated prior to use. The purpose of dry- or wet-heat is to destroy enzymes including beta-glucanase, lipase and lipoxygenase. Indeed, inactivation of lipase and lipoxygenase is indicated to prevent the product from turning rancid. In the process of the present invention heat treatment, in particular steaming, should be avoided or at least be kept as short as possible and/or carried out at a temperature as low as possible to keep oat protein denaturation low.

A preferred raw material used in the present invention to prepare oat seeds in step 1 is *Avena nuda*, naked oat or hulless oat, or dry milled oat flour, that have not been heat treated, in particular that have not been steamed. However, wet milled oat flour that has not been heat treated or dry milled flour of any oats fraction can also be used. Particularly preferred raw material is dry milled non-heat treated oats, non-heat treated oat bran, or non-steamed oats.

The second step aims to grind oat seeds in order to obtain protein rich flour. To grind oat seeds, all well-known common technologies can be used including stone-mill, roller mill or knife-mill. In this step, preferred particle size distribution of the resulting protein rich flour may be a D50 ($50^{th}$ percentile) above 30 microns, preferably above 40 microns, even more preferably above 50 microns. In the present invention, D50 is measured with help of any known by man skilled in the art technology. In a preferred way, laser granulometry is preferred.

The protein rich flour can comprise a protein content above 14%, e.g. above 16%, based on the dry solids content of the protein flour.

Preferably, the content of insoluble fiber in the protein rich flour is less than 4%, preferably less than 2%, based on the dry solids content of the protein flour. In these preferred ranges, the viscosity is lower during the process, which makes easier the conduction of the process.

In replacement of step 1 and 2 it is possible to use directly commercial oat flour. This alternative embodiment allows to merge step 1 and 2 of claim 1, which are done by a third-party, and to start quickly on step 3.

The third step aims to obtain a protein rich suspension which is an oat flour suspension. As water, every food compatible waters can be used but tap water and decarbonated water are preferred. The aim of this third step is to reach a dry matter comprised between 5% and 20%, preferably between 10% and 15%, most preferably between 10% and 13% by weight with respect to the total weight of the suspension. Preferably, in step 3, flour may be weighed and introduced in a tank containing water and equipped with agitation, pH and heating apparatus. Preferably, during step 3 temperature is regulated between 60° C. to 80° C., preferably between 65° C. and 75° C. Preferably, during step 3 pH is adjusted between 5 and 6, preferably 5,5. In the present application, pH can be adjusted by adding well-known acid or basic compounds such as hydrochloric acid, sodium hydroxide, citric acid, calcium hydroxide and potassium hydroxide. Agitation may be set-up in order to obtain a homogeneous suspension, without foaming.

The fourth step aims to hydrolyse the starch contained in the protein rich suspension with the help of amylases. Amylases are type of enzymes that catalyzes hydrolysis of starch molecules in smaller sugar molecules. In step 4 of the present application, every type of amylase can be used like beta-amylases or amyloglucosidase, but alpha-amylases are preferred. In a preferred embodiment, thermoresistant alpha-amylases are preferred.

The aim of step 4 is to efficiently reduce the size of starch contained in the protein rich suspension by hydrolysis, thereby obtaining a soluble dextrin or glucose syrup instead of starch. This soluble transformation of starch will allow a more simple separation with insoluble compounds in the coming steps. But, as exemplified below, such separation known from prior art is not effective to obtain a protein composition with less than 10% by weight of lipid based on the total dry weight of the protein composition.

In a preferred embodiment, alpha-amylase enzyme is preferred. Activity of alpha-amylase is expressed as KNU units. In practice, the α-amylase activity is measured using ethylidene-G7-PNP (4,6-ethylidene (G7)-p-nitrophenyl (G1)-α, D-maltoheptaoside) as a substrate. The compound is hydrolyzed by the LE399 alpha-amylase to G2-PNP and G3-PNP where G means glucose and PNP means p-nitrophenol. G2-PNP and G3-PNP are subsequently hydrolyzed by a-glucosidase, which is added to the reaction mixture, to glucose and p-phenol. Absorbance is measured spectrophotometrically at 409 nm under standard reaction conditions. One KNU (T) corresponds to the amount of [[α]]alpha-amylase that hydrolyzes 672 micromoles of ethylidene-G7PNP per minute under standard conditions (pH 7.1; 37° C. The quantification limit of the method is approximately 0.3 KNU (T)/g. In the step 4, amylase added in step 4 may have an activity level comprised between 100 and 170 KNU/100 g of flour, preferably between 110 and 160 KNU/100 g of flour, even more preferably between 120 and 150 KNU/100 g of flour. In other words, alpha-amylase units quantities introduced in order to hydrolyze starch are comprised between 100 and 170 KNU/100 g of flour, preferably between 110 and 160 KNU/100 g of flour, even more preferably between 120 and 150 KNU/100 g of flour. One Kilo Novo alpha-amylase Unit (KNU) is a value known by the man skilled in the art and is the amount of enzyme which breaks down a determined quantity of starch per hour at Novozymes' standard method. This tests consists in determining alpha-amylase activity relative to an alpha-amylase standard with known activity (Termamyl) and is expressed in Kilo Novo alpha-amylase Units (KNU). One KNU is the amount of alpha-amylase which, under standard conditions (pH 7.1; 37° C.), dextrinizes 5.26 g starch dry substance per hour.

The fifth step consists in an optional centrifugation separating a heavy layer comprising fibers and a light layer comprising proteins. Indeed, as fibers and starch are insoluble and heavier than proteins, sugar and salts, they will be separated with help of a centrifuge which preferably operates between 3000 G and 4000 G.

As exemplified below, more than 70% of the dry matter, preferably more than 80% of the dry matter obtained after step 5 is constituted of proteins.

The sixth step consists in an addition of polysorbate.

Polysorbates are a class of emulsifiers used in cosmetic, pharmaceuticals and food preparations. Polysorbates are oily liquids derived from ethoxylated sorbitan (a derivative of sorbitol) esterified with fatty acids. Common brand names for polysorbates include Scattics (polysorbate), Alkest (polysorbate), Canarcel (polysorbate), and Tween (polysorbate). Common used polysorbate are Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate) and Polysorbate 80 (polyoxyethylene (20) sorbitan monooleate) (number following 'polyoxyethylene' refers to total number of oxyethylene-(CH2CH2O)-groups found in the molecule and number following 'polysorbate' is related to the type of fatty acid associated with the polyoxyethylene sorbitan part of the molecule). Preferably, the polysorbate is Polysorbate 80 (polyoxyethylene (20) sorbitan monooleate) also known as Tween (polysorbate) 80.

After hydrolysis of step 4, and optionally removal of internal fibers in step 5, and before addition of polysorbate in step 6, pH may be adjusted between 5,5 and 7,5, preferably 6,5. In step 6, the polysorbate may be added at temperature comprised between 50° C. and 80° C., preferably between 55° C. and 75° C., and even more preferably 65° C.

Polysorbate may be added at a percentage comprised between 0.5% and 5%, preferably between 2% and 4%, and more preferably 3% by weight with respect to the total weight of protein rich flour which is an oat flour.

Polysorbate 80 is preferred, example of commercial Polysorbate 80 is Tween 80 from CRODA Medium may then be agitated under stirring and preferably for an average hour.

Seventh step consists in a centrifugation allowing separation of a protein rich suspension in a heavy layer containing mainly protein and a light layer containing others compounds including lipids.

In a preferred embodiment, during step 7 pH is first adjusted between 4 and 6, preferably 6. By adjusting pH at this range, proteins will coagulate. In a preferred embodiment, heat may also be applied to help to coagulate. In this case, temperature will be set between 40° C. and 70° C., preferably between 50° C. and 60°. In all embodiments, the duration of step 7 is chosen to reach a sufficient coagulation. Preferably, the duration of step 7 is sets between 30 min and 2 hours, preferably between 45 min and 1 hour. Then medium is fed in a centrifuge which may operate between 3000 G and 4000 G. The pellet, lower part or heavy layer, which contains proteins is collected. The supernatant, higher layer or light layer, which contains hydrolyzed starch and lipids is discarded.

In a preferred embodiment, the pellet, lower part or heavy layer is mixed with water, agitated and then fed in a second centrifuge which may operate between 3000 G and 4000 G. Once again, the pellet, lower part or heavy layer, which contains proteins is collected. The supernatant, higher layer or light layer, which contains hydrolyzed starch and lipids is discarded.

In a last eighth optional step, oat protein concentrated in the pellet, lower part or heavy layer, can be dried. In order to do so, man skilled in the art may preferably use a spray-drier, preferably a multistage spray-drier. This will allow to provide an oat protein composition having the mean particle size defined hereabove. Before spray-drying, homogenization and a UHT treatment step can also be done.

A third and last embodiment of the present invention is the use of protein composition of the present invention or obtained by the process of the present invention, preferably in food, feed, pharmaceutical and cosmetic fields.

Such oat protein composition is particularly suitable for ready to drink, beverages, baking. Its low lipid content allows an improved organoleptic experience when formulated, as with low lipid content and in presence of oxygen no undesirable compounds can alter its organoleptic quality.

Invention will be better understood with the following non-exhaustive examples.

EXAMPLES

Method for Determining MW Distribution:

Samples were dissolved in 200 mM phosphate buffer, pH=7.6, vortexed for 1 minute initially and 10 minutes later and stored at 4 C over-night. The solutions were centrifuged at 7000 g for 10 minutes, the supernatant was measured for soluble protein content the next day, and the samples were diluted to 10 mg/mL with phosphate buffer.

The samples were chromatographed using 2 SEC columns (400 and 300 Agilent Advanced Bio SEC Column, 5000-1, 250,000 MW Range) in sequence using phosphate buffer, pH=7.6 as the mobile phase at 0.5 mL/minute. The detection was a UV=280 nm.

Several protein molecular weight standards going from 14300 to 669000 Da (Lysozyme, Carbonic Anhydrase, BSA, HSA, B-Amylase, Apoferritin, Thyroglobulin) were analyzed to identify the retention time and calibrate the chromatography apparatus.

For sample analysis, chromatograms peak or peak apex (group) was determined along with the range of the peak (start and end) and the molecular weight was determined for the range and peak apex. The percent of molecular weight was determined for: >300 kDa, 300 kDa to 50 kDa, 50 KDa to 10 KDa and <10 kDa.

Example 1: Prior Art Process Involving Starch Hydrolysis

Weigh 2.5 kg N°70 oat flour from Grain Millers, Lot no. 1802150. Fill a feed tank with 25 L water at 40-50° C. Mix flour into water. Adjust pH to 5.4 to 5.5 with 1 N HCl while agitating for 10 min. Add 25 g Liquozyme (alpha-amylase) supra (from Novozyme (alpha-amylase)). Heat on hot plate 70° C., 300 rpm, for 2 hours. Reduce pH to 5.0 with 1 N HCl and stir for 30 min. Feed through a Lemitec centrifuge at 500 mL/min, 580 G, 10 rpm differentia. Add 12.5 L 50° C. water to the curd. Adjust to pH 5.0 with 1 N HCl. Feed through Lemitec 500 mL/min, 3600 rpm, 10 rpm differential. Dry washed curd with spray-dryer.

Sample is called "S1: Prior art without polysorbate"

Example 2: Inventive Process Involving Starch Hydrolysis and Use of Polysorbate Weigh 2.5 kg N°70 oat flour from Grain Millers, Lot no. 1802150. Fill a feed tank with 25 L water, 40-50° C. Mix flour into water. Adjust pH to 5.4 to 5.5 with 1 N HCl while agitating for 10 min. Add 25 g Liquozyme (alpha-amylase) supra (from Novozyme (alpha-amylase)). Heat on hot plate 70° C., 300 rpm, for 2 hours. Add 75 g of Tween 80. Adjust pH to 6,5 and allow to cool to 65° C., hold 60 min. Reduce pH to 5.0 with 1 N HCl and stir for 30 min. Feed through Lemitec centrifuge 500 mL/min, 580 G, 10 rpm differentia. Add 12.5 L 50° C. water to the curd. Adjust to pH 5.0 with 1 N HCl. Feed through Lemitec 500 mL/min, 3600 rpm, 10 rpm differential. Dry washed curd with spray-dryer.

Sample is called "S2: Invention with polysorbate"

Example 3: Importance of Choice of Polysorbate as Surfactant

Polysorbate will be compared to sodium dodecylsulfate, another well-known food surfactant.

Weigh 2.5 kg N°70 oat flour from Grain Millers, Lot no. 1802150. Fill a feed tank with 25 L water, 40-50° C. Mix flour into water. Adjust pH to 5.4 to 5.5 with 1 N HCl while agitating for 10 min. Add 25 g Liquozyme (alpha-amylase) supra (from Novozyme (alpha-amylase)). Heat on hot plate 70° C., 300 rpm, 2 hours. Add 75 g of SDS. Adjust pH of SDS sample to 6, allow to cool to 65° C., hold 60 min. Reduce pH to 5.0 with 1 N HCl and stir for 30 min. Feed through Lemitec centrifuge 500 mL/min, 580 G, 10 rpm differentia. Add 12.5 L 50° C. water to the curd. Adjust to pH 5.0 with 1 N HCl. Feed through Lemitec 500 mL/min, 3600 rpm, 10 rpm differential. Dry washed curd with spray-dryer.

Sample is called "S3: comparative example with SDS"

Example 4: Importance of Parameter Reaction with Polysorbate

Weigh 2.5 kg N°70 oat flour from Grain Millers, Lot no. 1802150. Fill a feed tank with 25 L water, 40-50° C. Mix flour into water. Adjust pH to 5.4 to 5.5 with 1 N HCl while agitating for 10 min. Add 25 g Liquozyme (alpha-amylase) supra (from Novozyme (alpha-amylase)). Heat on hot plate 70° C., 300 rpm, for 2 hours. Add 75 g of Tween 80. Adjust pH to 6,5 and allow to cool to 35° C., hold 60 min. Reduce pH to 5.0 with 1 N HCl and stir for 30 min. Feed through Lemitec centrifuge 500 mL/min, 580 G, 10 rpm differentia. Add 12.5 L 50° C. water to the curd. Adjust to pH 5.0 with 1 N HCl. Feed through Lemitec 500 mL/min, 3600 rpm, 10 rpm differential. Dry washed curd with spray-dryer.

Sample is called "S4: polysorbate treatment at suboptimal condition"

Example 5: Preferred Embodiment with Use of Fiber Centrifugation Before Use of Polysorbate Weigh 2.5 kg of N°70 oat flour from Grain Millers, Lot no. 1802150. Fill a feed tank with 25 L water, 40-50° C. Mix flour into water. Adjust pH to 5.4 to 5.5 with 1 N HCl while agitating for 10 min. Add 25 g Liquozyme (alpha-amylase) supra (from Novozyme (alpha-amylase)). Heat on hot plate 70° C., 300 rpm, 2 hours. Adjust pH to 7.0 with 1 N NaOH. Centrifuge with a Lemitec centrifuge 580 G, 10 rpm diff, 500 ml/min, with 60/10 weir. Add 75 g of Tween 80 to overflow. Adjust pH to 6, allow to cool to 65 C, hold 60 min. Reduce pH to 5.0 with 1 N HCl. Feed through Lemitec centrifuge 580 G, 3600 rpm, 10 rpm differentia. Add 12.5 L 50° C. water to the curd. Adjust to pH 5.0 with 1 N HCl. Feed through Lemitec 500 mL/min, 3600 rpm, 10 rpm differential. Dry washed curd with spray-dryer.

Sample is called "S5: use of fiber centrifugation before use of polysorbate"

Example 6: Comparison of Previous Examples

Results are presented in Table 1 below. In Table 1, percentages are expressed as percentages by weight using the methods described hereabove. D50 is measured by a laser granulometry apparatus (Mastersizer 3000 (particle size analyzer), from Malvern), which measures intensity of scattered light across a range of scattering angles using forward scattering measurement, on a dry powder without dispersion buffer, and using the software of the apparatus with the Mie scattering model to fit the distribution to the measured scattering pattern.

TABLE 1

| | Protein (%) | Lipid (%) | Dry matter (%) | D50 (microns) |
|---|---|---|---|---|
| S1: Prior art without polysorbate | 54.4 | 15.9 | 2.6 | — |
| S2: Invention with polysorbate | 57 | 6.2 | 1.3 | 55 |
| S3: comparative example with SDS | 41 | 10.3 | 1 | — |
| S4: polysorbate treatment at suboptimal condition | 68.4 | 10.4 | 1 | — |
| S5: use of fiber centrifugation before use of polysorbate. | 75 | 6 | 1.1 | 51 |

Example 7: Production of Oat Protein Composition at Pilot Scale

The protein composition was produced using the following protocol:

Weigh 12.5 kg oat flour (no 70 Grain miller), fill 50 gall jacketed tank with approximately 88 L of 50° C. water and mix flour into water, adjust to achieve 12% solids. Adjust pH to 5.4 to 5.5 with HCl while agitating for 10 min and add 125 g Liquozyme (alpha-amylase) supra (from Novozyme (alpha-amylase)). Heat to 70 C with heat exchanger, using recirculation pump, during 2 hours. Then adjust pH to 7.0 with NaOH and centrifuge 5000 rpm, 10 rpm diff, 2000 ml/min feed to Lemitec decanter centrifuge, with 60/10 weir, and collect overflow in a 50 gallons tank. Add 210 g of 30% solution Tween 80 to the tank (62.5 g pure T80) and heat to 65° C. and hold 60 min. Fill tank to capacity with water, heat back to 60° C. and reduce pH to 5.0 with HCl. Centrifuge on Clara 20 disc centrifuge, 0.45 $m^3$/h, 9,000 rpm. Resuspend underflow fraction in jacketed 50 gal tank, fill to capacity with water and heat to 60° C., repeat centrifugation step and store underflow fraction in 5 gal bucket overnight in fridge. Heat to 40° C., adjust at pH 7.0 and pass through ultra-high temperature apparatus (at 154° C. hold temperature, 71° C. flash temperature, 15 s hold time (380 ml/min, pp speed 200, long loop). Dry with spray-dryer.

The oat protein composition comprises 82.8% protein, 6.1% lipids, 1.5% of insoluble fiber, 1.6% of soluble fiber, 1.7% of beta-glucans and 3.3% of moisture. The starch content is determined to be around 2-3%. The distribution of MW is indicated in the Table 2 below.

TABLE 2

| Distribution MW | % |
|---|---|
| % MW >300 KD | 10.64 |
| % MW 300 KD to 50 KD | 52.69 |
| % MW 50 KD to 10 KD | 32.98 |
| % MW <10 KD | 3.69 |

The invention claimed is:

1. An oat protein composition wherein said composition does not contain traces of organic solvent, has residual lipid content below 10% by weight on dry matter based on the total dry weight of the oat protein composition and has a mean particle size (d 50), determined by laser diffraction, greater than 10 microns; and wherein said oat protein composition comprises, based on the total weight of proteins in the composition:

from 5 to 15% of proteins having a molecular weight of 300 kDa and more, from 45 to 65% of proteins having a molecular weight of between 50 and 300 kDa, from 25 to 45% of proteins having a molecular weight of between 10 and 50 kDa, from 1 to 10% of proteins having a molecular weight of 10 kDa and less, the sum making 100%.

2. The oat protein composition as defined in claim 1 wherein said oat protein composition contains from 40% to 70% by weight of protein on dry matter based on the total dry weight of the oat protein composition.

3. The oat protein composition as defined in claim 1 wherein said oat protein composition contains more than 70% by weight of protein on dry matter based on the total dry weight of the oat protein composition.

4. The oat protein composition as defined in claim 1 wherein the oat protein composition comprises from 0.1 to 10% by weight of starch on dry matter based on the total dry weight of the oat protein composition.

5. The oat protein composition as defined in claim 1 wherein the oat protein composition comprises a total dietary fiber going from 0.1 to 10% by weight of the dietary fiber on dry matter based on the total dry weight of the oat protein composition.

6. The oat protein composition as defined in claim 1 wherein the oat protein composition has:

a mean particle size greater than 20 microns, and a mean particle size lower than 300 microns.

7. The oat protein composition as defined in claim 1 wherein said oat protein composition contains from 50% to 60% by weight of protein on dry matter based on the total dry weight of the oat protein composition.

8. The oat protein composition as defined in claim 1 wherein said oat protein composition contains more than 80% by weight of protein on dry matter based on the total dry weight of the oat protein composition.

9. The oat protein composition as defined in claim 1 wherein the oat protein composition comprises from 1 to 4% by weight of starch on dry matter based on the total dry weight of the oat protein composition.

10. The oat protein composition as defined in claim 1 wherein the oat protein composition comprises a total dietary fiber from 1 to 4% by weight of the dietary fiber on dry matter based on the total dry weight of the oat protein composition.

11. The oat protein composition as defined in claim 1 wherein the oat protein composition has:

a mean particle size greater than 40 microns, and a mean particle size lower than 150 microns.

12. A food, a feed, a pharmaceutical or a cosmetic comprising the oat protein composition as defined in claim 1.

* * * * *